(12) United States Patent
Salter et al.

(10) Patent No.: US 7,897,365 B2
(45) Date of Patent: Mar. 1, 2011

(54) METHOD FOR ADJUSTING ANTIBIOTIC SENSITIVITY OF A TEST CULTURE

(75) Inventors: Robert S. Salter, Reading, MA (US); Steven J. Saul, Arlington, MA (US); Martin T. Rossi, Methuen, MA (US); Robert J. Markovsky, Brentwood, NH (US)

(73) Assignee: Charm Sciences, Inc., Lawrence, MA (US)

( * ) Notice: Subject to any disclaimer, the term of this patent is extended or adjusted under 35 U.S.C. 154(b) by 112 days.

(21) Appl. No.: 10/578,935

(22) PCT Filed: Nov. 5, 2004

(86) PCT No.: PCT/US2004/037220
§ 371 (c)(1), (2), (4) Date: May 9, 2006

(87) PCT Pub. No.: WO2005/049809
PCT Pub. Date: Jun. 2, 2005

(65) Prior Publication Data
US 2007/0148724 A1 Jun. 28, 2007

Related U.S. Application Data

(60) Provisional application No. 60/523,065, filed on Nov. 18, 2003, provisional application No. 60/574,252, filed on May 25, 2004.

(51) Int. Cl.
*C12Q 1/18* (2006.01)
(52) U.S. Cl. ....................................................... 435/32
(58) Field of Classification Search .................... 435/32
See application file for complete search history.

(56) References Cited

U.S. PATENT DOCUMENTS

| | | | |
|---|---|---|---|
| 3,941,658 A | 3/1976 | Lameris et al. | |
| 4,239,745 A * | 12/1980 | Charm | ....................... 436/501 |
| 4,239,852 A | 12/1980 | Charm | |
| 4,929,546 A | 5/1990 | Mayra-Makinen | |
| 4,946,777 A | 8/1990 | Lameris et al. | |
| 5,354,663 A | 10/1994 | Charm et al. | |
| 5,434,053 A | 7/1995 | Piasio | |
| 5,489,532 A | 2/1996 | Charm et al. | |
| 5,494,805 A | 2/1996 | Van Rijn et al. | |
| 5,658,748 A | 8/1997 | Mayra-Makinen et al. | |
| 6,180,395 B1 | 1/2001 | Skiffington et al. | |
| 6,319,466 B1 * | 11/2001 | Markovsky et al. | ............ 422/56 |
| 6,867,015 B1 * | 3/2005 | Langeveld et al. | ............. 435/29 |
| 7,229,783 B2 * | 6/2007 | Saul et al. | ..................... 435/31 |
| 2007/0190592 A1 * | 8/2007 | Black et al. | ................... 435/32 |

FOREIGN PATENT DOCUMENTS

| | | |
|---|---|---|
| EP | 0593112 A1 | 4/1994 |
| EP | 0861330 B1 | 8/2003 |
| WO | WO-94/18343 | 8/1994 |
| WO | WO-01/25471 A2 | 4/2001 |
| WO | WO-01/25795 A2 | 4/2001 |
| WO | WO-2004/086979 A1 | 10/2004 |
| WO | WO-2005/024048 A1 | 3/2005 |

OTHER PUBLICATIONS

Frederic W. Douglas Jr, Rae Greenberg, Harold M. Farrell Jr. & Locke F. Edmondson, Effects of Ultra-High-Temperature Pasteurization on Milk Proteins, Journal Agric. Food Chem, 1981, vol. 29, No. 1, American Chemical Society, United States, pp. 11-15.
S.L. Stead, M. Sharman, J. Stark, & E.M.L. Geijp, Improvements to the Screening of Antimicrobial Drug Residues in Food by the use of the PremiTest.
Performing the Fast Antimicrobial Screen Test, Medtox Diagnostics, Inc. NC pp. 1-9.
J.M.B. Musser, K.L. Anderson, J.E. Rushing, & W.A. Moats, Potential for Milk Containing Penicillin G or Amoxicillin to Cause Residues in Calves, J. Dairy Sci, 84:1pp. 126-133, American Dairy Association, 2001.
Product Information: COPAN (CH-ATK) Antibiotic Test Kit Jul. 2001.

* cited by examiner

*Primary Examiner* — Ralph Gitomer
(74) *Attorney, Agent, or Firm* — MacCord Mason PLLC (57) ABSTRACT

The present invention relates to a method for adjusting the sensitivity of a microbial culture to an antibiotic. The method employs a substance derived from a bacterial species with sensitivity to the antibiotic. Such bacterial species include the same species used in the culture or a different species.

29 Claims, 7 Drawing Sheets

METHOD FOR ADJUSTING ANTIBIOTIC SENSITIVITY OF A TEST CULTURE

REFERENCE TO PRIOR APPLICATIONS

This application is based on and claims priority from U.S. Provisional Patent Application No. 60/523,065, filed Nov. 18, 2003, and U.S. Provisional Patent Application No. 60/574,252, filed May 25, 2004, both of which are hereby incorporated by reference.

BACKGROUND

Antibiotics used in animal feed or to treat farm animals, such as dairy and beef cattle and swine, occasionally contaminate the food supply. The hazards associated with these undesirable residues include allergic reactions, propagation of resistant organisms and other long-term health risks. As a result, government agencies such as the United States Department of Agriculture and the United States Food and Drug Administration require monitoring of such residues in foods. Foods such as milk, meat, poultry, seafood and animal feed are routinely tested for the presence of such residues. We disclose herein a user-friendly method for detecting a variety of residues in a single, broad-spectrum test.

Various animal parts and excretions can be tested for the presence of antibiotics. Tests for antibiotics in kidney include tests for hog kidney and veal bob kidney. Problems with some of the available tests, particularly in the pork industry, include sensitivities that do not match well with governmental or industry limits. Some tests are over-sensitive to certain antibiotics and under-sensitive to others.

Sensitivities of currently available microbial growth inhibition tests, are based primarily on parameters that affect test sensitivity to all drugs. Such parameters include growth organism used, amount or concentration of growth organism used, vessel dimensions, media volume, media type, mix of nutrients, incubation time and temperature. As a result, if a test is adequately sensitive to some drugs, but overly sensitive to other drugs, other methods for sensitivity adjustment may be needed.

Another problem with some tests is that they may require cumbersome extraction procedures or use of organic solvents that must be removed from the sample prior to test operation. This adds a cumbersome procedural step. Some tests are also procedurally cumbersome, requiring incubation of a sample swab on a lawn of bacterial culture and inoculation of an agar surface with spores just prior to running the test.

In addition to problems with slow testing time, over-sensitivity, under-sensitivity and extraction, none of the currently available tests are provided in an all-in-one format in which all test reagents and sampling devices are provided in one test instrument.

SUMMARY

We disclose herein various embodiments of a test apparatus and method to detect antibiotics in a test sample using growth inhibition of a microbial culture. Some embodiments include all of the reagents for a microbial culture in a ready-to-use format. The culture can include, for example, nutrients, agar, one or more buffers, spores and color indicator. Alternatively, any one or more of such components can be provided separately, for example in a separate reagent compartment hereinafter referred to as a "niblet". In an embodiment of the ready-to-use format, the user only has to add the sample, or sample extract, and incubate for a prescribed time period, for example about 1.5 to 4 hours, at a prescribed temperature, for example about 55-70 degrees C., and observe the results.

If extraction is required, an extractant can be provided separately from the other reagents. In an example the extractant is in a niblet. The niblet containing the extractant can be included in a test unit including other test components. The test unit can include the niblet contained within a vial attached to the bottom of the test unit. The seals of the niblet can be puncturable membrane seals such as metallic foil seals or foil-like seals or plastic or plastic-like seals. Puncturing the seals allows the extractant to contact the culture. The user only has to add the sample to the extractant, contact the extracted sample with the culture, and incubate for the prescribed time period at the prescribed temperature. The extractant can be a buffer solution capable of extracting antimicrobial drugs from a kidney sample, such as a bovine or porcine kidney sample. The extractant can also be a reagent for merely removing the sample from a swab and transferring the sample into the culture.

Some embodiments include two or more buffers (hereinafter referred to as a polybuffer) having multiple pKa values. A polybuffer can improve pre-test and/or post-test stability of the culture and other aspects of test performance. Post-test stability allows results to be retained at room temperature for an extended period, for example 6-8 hours or more, without a change in test result. The polybuffer can be premixed within the culture or provided separately such as in a niblet for later addition.

An embodiment includes reducing sensitivity of the microbial culture to certain inhibitors of culture growth. In some growth inhibition assays, the inhibition of microbial culture by antibiotics from a sample, or reversal of such inhibition, can be used as an antibiotic screening mechanism. The sensitivity of such tests can be adjusted by contacting the culture with at least one adjustment reagent. Examples of adjustment reagents include binding protein, enzyme, chemical analogue and/or antibodies that bind to, or otherwise inhibit the effectiveness of, antibiotics. The adjustment reagent can be used to adjust the sensitivity of the test for at least one antibiotic or other culture growth inhibitor. An example of a microbial enzyme useful as an adjustment binder is an antibiotic receptor/binder from the cell wall of microbes such as Bacillus (Geobacillus) Stearothermophilus (B. st.). The adjustment reagent can be applied in a variety of ways, for example combined within a culture or broth, applied on top of a solid culture, such as an agar matrix, added on a sample swab or contained in a dilution buffer.

Possible adjustment reagents include antibiotic receptors/binders isolated from bacteria, monoclonal and polyclonal antibodies. When the adjustment reagent is an antibiotic binder, such as a binding protein, for example a bacterial antibiotic receptor or antibody, the adjustment reagent can reduce the availability of antibiotics capable of inhibiting the growth of the particular culture used, such as by binding to the antibiotic. Similarly, adjustment reagents can include substances that, rather than bind with the antibiotic, reduce the influence of the antibiotic on the growth organism.

Some embodiments include a test apparatus with a solid or semi-solid culture within a vial. The culture can include all or some of the test biochemicals including agar, nutrients, color indicators, one or more buffers and spores. In an embodiment, the culture, prior to the addition of test sample, is adjusted to a pH of greater than about 8. Such a pH can help avoid culture contamination, for example with mold, and lengthen pre-testing shelf-life. The vial can include a sealed bottom end and a membrane seal over the top end. In test operation the user can puncture the seal with, for example, a pipette tip or swab and then dispense the sample, for example a 200 microliter sample of milk, into the vial.

Some embodiments include the complete test unit containing all of the reagents, premixed together and ready for use in a culture and, in addition, a sampling instrument, such as a swab or probe and optional extractant. The probe can be used to puncture the one or more seals separating the optional extractant from the culture. The probe can be used to absorb and apply the sample to the reagents within the test apparatus and can comprise an absorbent material such as an absorbent, fibrous, cotton-like or cotton material. An example of such a sampling instrument is a swab or probe in the format of a POCKETSWAB (POCKETSWAB is a registered trademark of Charm Sciences, Inc. Lawrence, Mass.). The format of the POCKETSWAB provides the advantage of controlled movement of the swab in a test device that provides physical support for the swab. For example, the swab can be controllably moved into the reagent compartment containing an extraction buffer. Using the POCKETSWAB device the swab can remain in the extractant for the time desired. In addition to the convenience of delivering the swab to the customer in an all-in-one device, the POCKETSWAB provides the physical support so that the swab will remain within the extractant or buffer solution without the user providing external support to the swab while soaking. After sample extraction, the swab or swab tip is moved longitudinally through a seal thereby allowing the sample to flow onto or into the culture.

In a particular embodiment, the test method is used to reduce sensitivity of a microbial culture to the beta-lactam family of antibiotics. A beta-lactam binding protein is used to selectively reduce test sensitivity to the beta-lactams. Test sensitivity will be mostly unaffected relative to antibiotics or inhibitors other than beta-lactams. In an embodiment, the beta-lactam binder is a receptor from *B.st.* and the culture is made of spores of *B.st.*

BRIEF DESCRIPTION OF THE DRAWINGS

FIGS. 1-9 are drawings depicting an embodiment in which the POCKETSWAB format is used.

FIG. 11 and FIG. 12 are perspective drawings of an embodiment in which multiple vials are supplied for multiple samples. Perforation or other detachable attachments allow the user to determine the number of tests to run at one time. Within the bottom portion of each vial assembly 4 is the culture 15. The optional niblet assembly 5 can also be provided. At the top of the vial assembly 4 there is a puncturable covering 12 which can be, for example, a puncturable membrane or foil seal. The vial assembly 4 can also be threaded 9 for optional attachment to the POCKETSWAB test apparatus or for easy capping. In test operation a swab or pipette tip can be used to puncture the seal 12 on top of the vial 4 prior to application of test sample to the culture 15. If the niblet assembly 5 is also provide within the vial assembly 4, a pipette tip can be used to mix the sample with the reagents within the niblet assembly 5 and to puncture the various seals.

DETAILED DESCRIPTION

Figure 1:
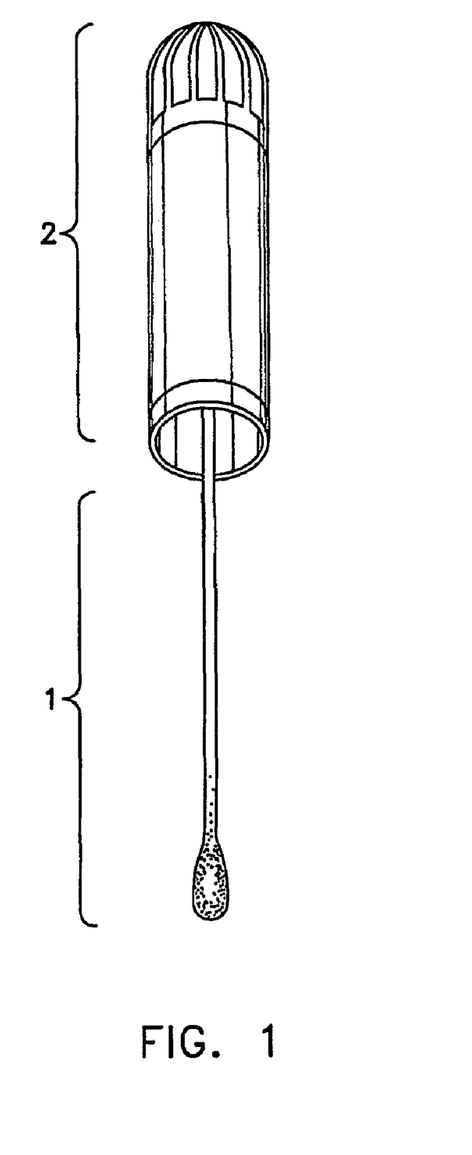
FIG. 1 is an exploded perspective drawing of a swab 1 attached to a swab handle 2. The swab 1 is used to obtain a sample.
Figure 2:
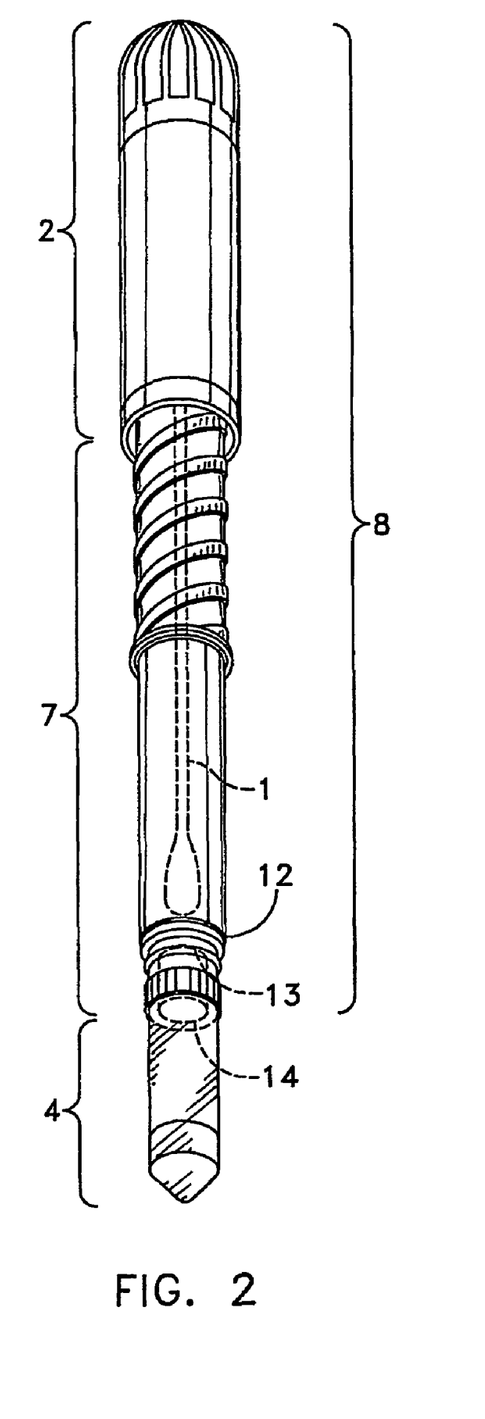
FIG. 2 is an exploded perspective drawing of the whole POCKETSWAB assembly 8 with the swab 1 in the pre-use position within the swab body 7.
Figure 3:
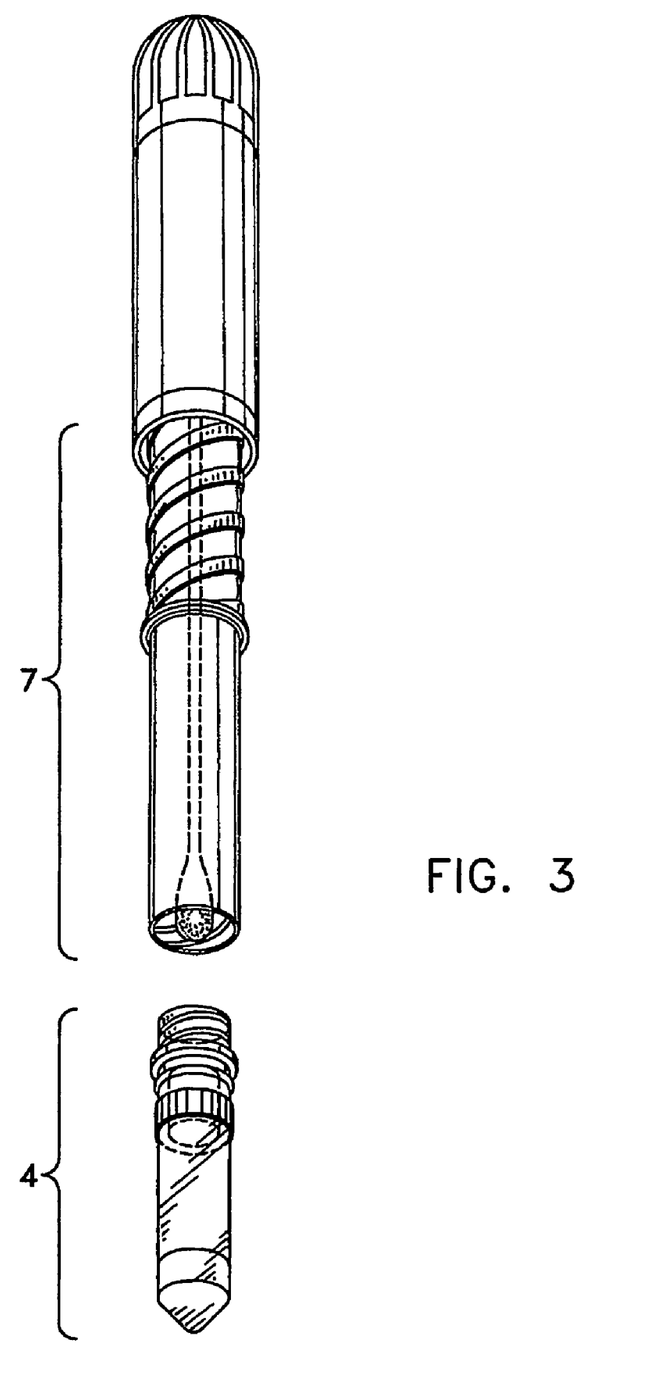
FIG. 3 is an exploded perspective showing the vial assembly 4 removed from the POCKETSWAB body 7.
Figure 4:
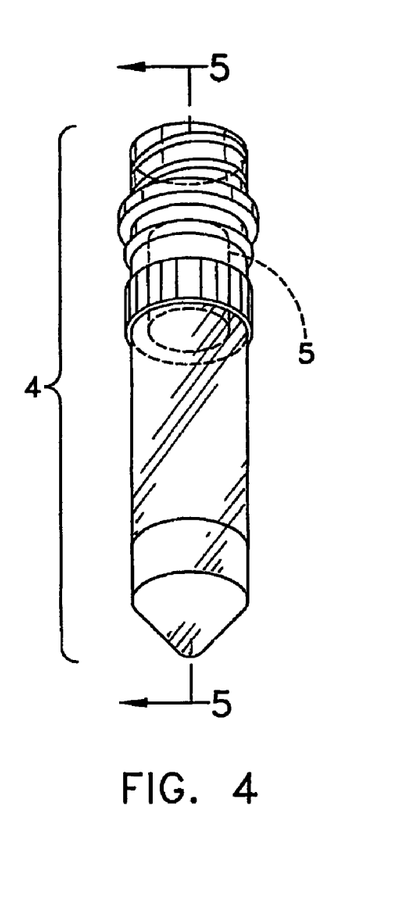
FIG. 4 is an exploded perspective drawing of the vial assembly 4 showing cross-sectional lines 9 and niblet 5.
Figure 5:
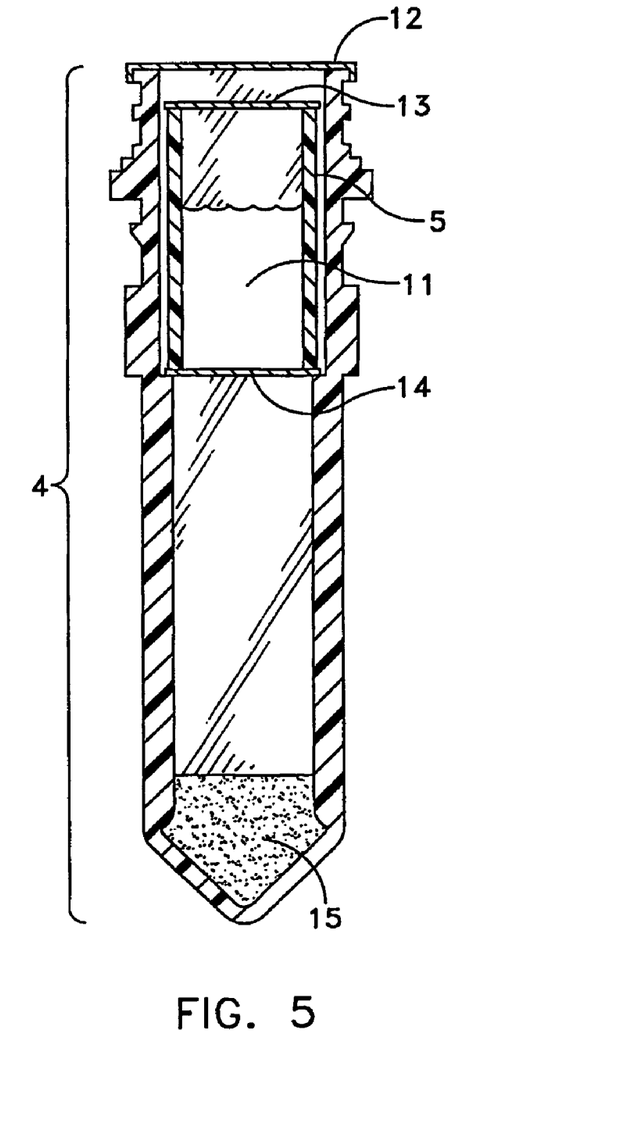
FIG. 5 is a cross-sectional view of the assembly shown in FIG. 4 with culture 15 at bottom of vial 4 below niblet 5 with extractant 11 or other additional reagent sealed therein.
Figure 6:
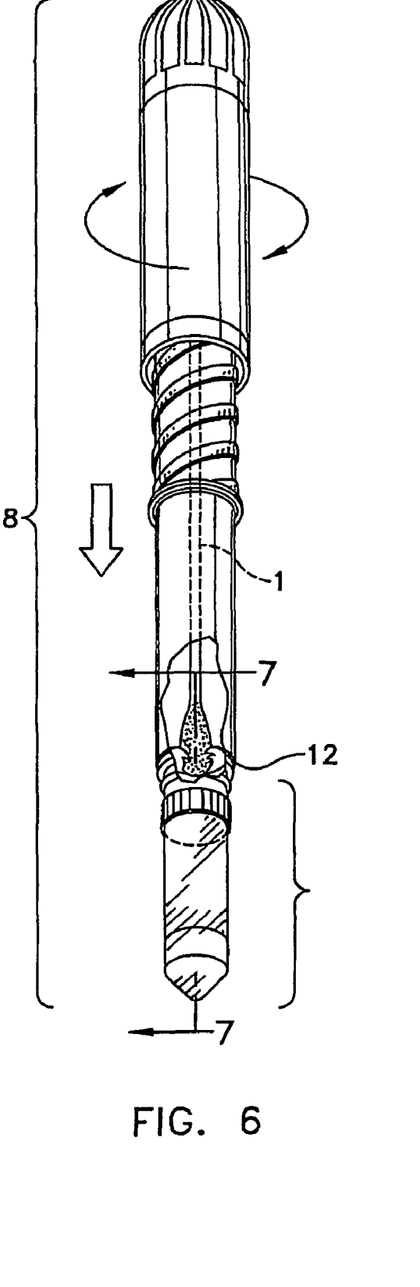
FIG. 6 is an exploded perspective drawing of the in-use POCKETSWAB assembly 8 in which the sample has been obtained and the swab 1 is moved through the seal 12 covering the vial assembly 4.
Figure 7:
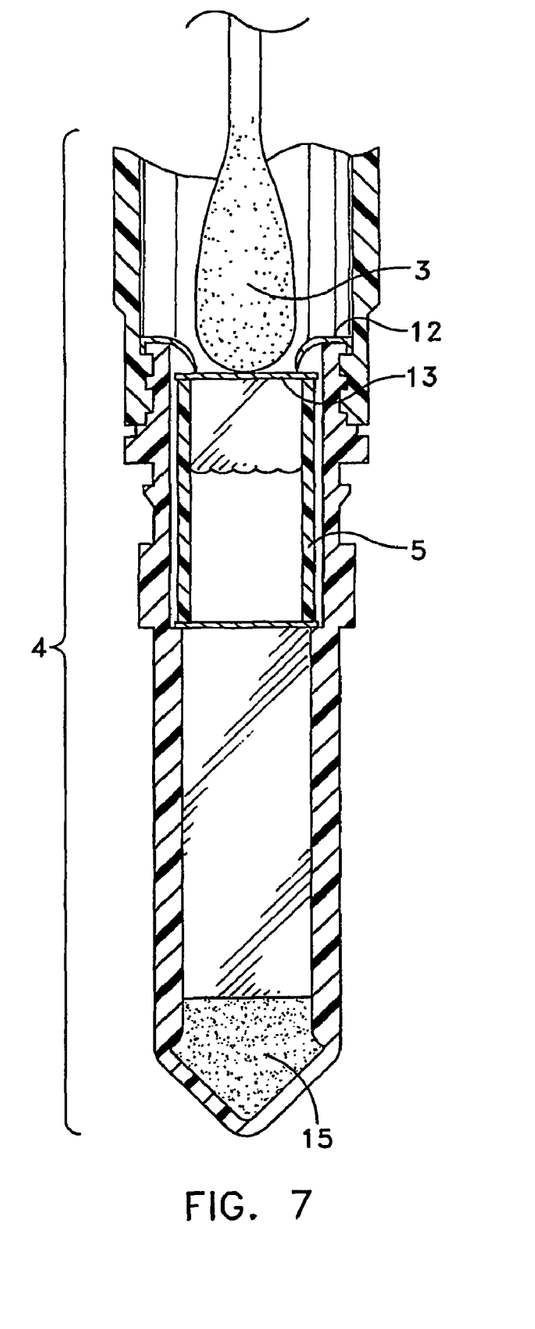
FIG. 7 is a cross-sectional view of the assembly shown in FIG. 6. The swab tip 3 has broken through the seal 12 covering the vial assembly 4. The seal 13 on the top end of the niblet assembly 5 has not yet been punctured.
Figure 8:
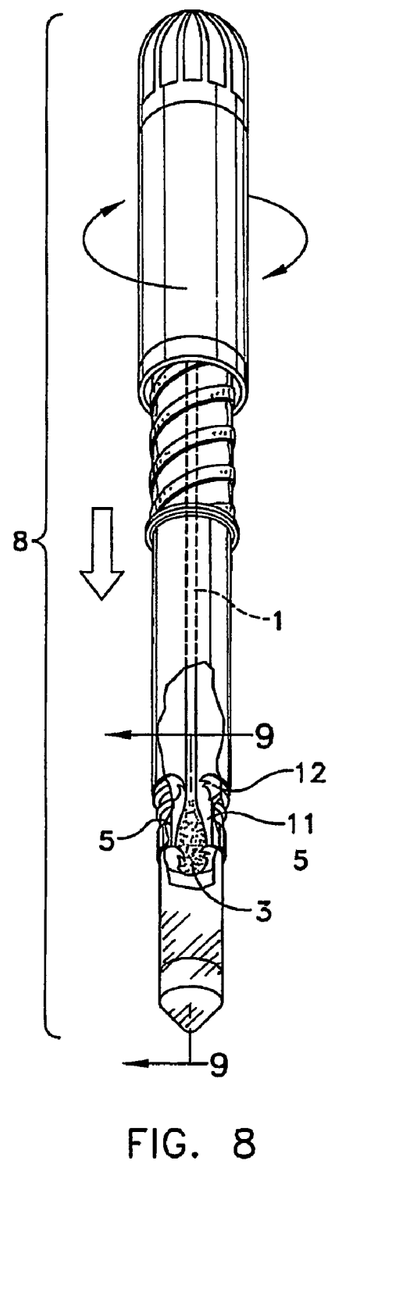
FIG. 8 is an exploded perspective drawing of the in-use POCKETSWAB assembly 8 in which the sample has been obtained and the swab 1 is moved through the seal 12 covering the vial assembly 4 and the seal 13 covering the top end of the niblet assembly 5 to contact the reagent 11 within the niblet assembly 5.
Figure 9:
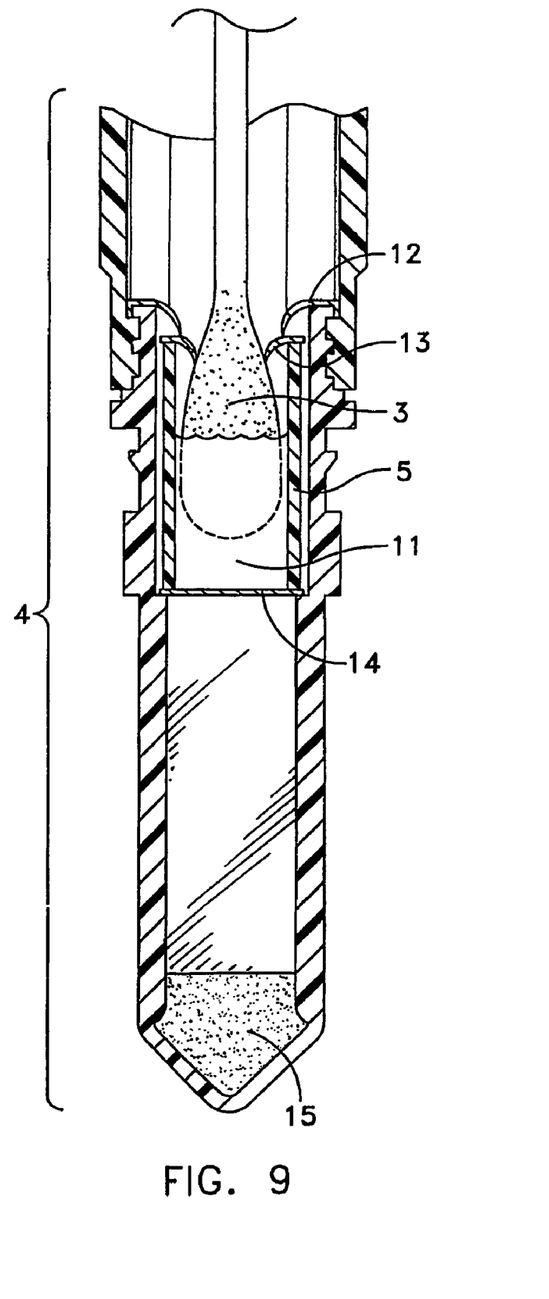
FIG. 9 is a cross-sectional view of the assembly shown in FIG. 8. The swab tip 3 has broken through the seal 12 covering both the vial assembly 4 and the seal 13 on the top end of the niblet assembly 5. The seal 14 on the bottom end of the niblet assembly 5 has not yet been punctured.
Figure 10:
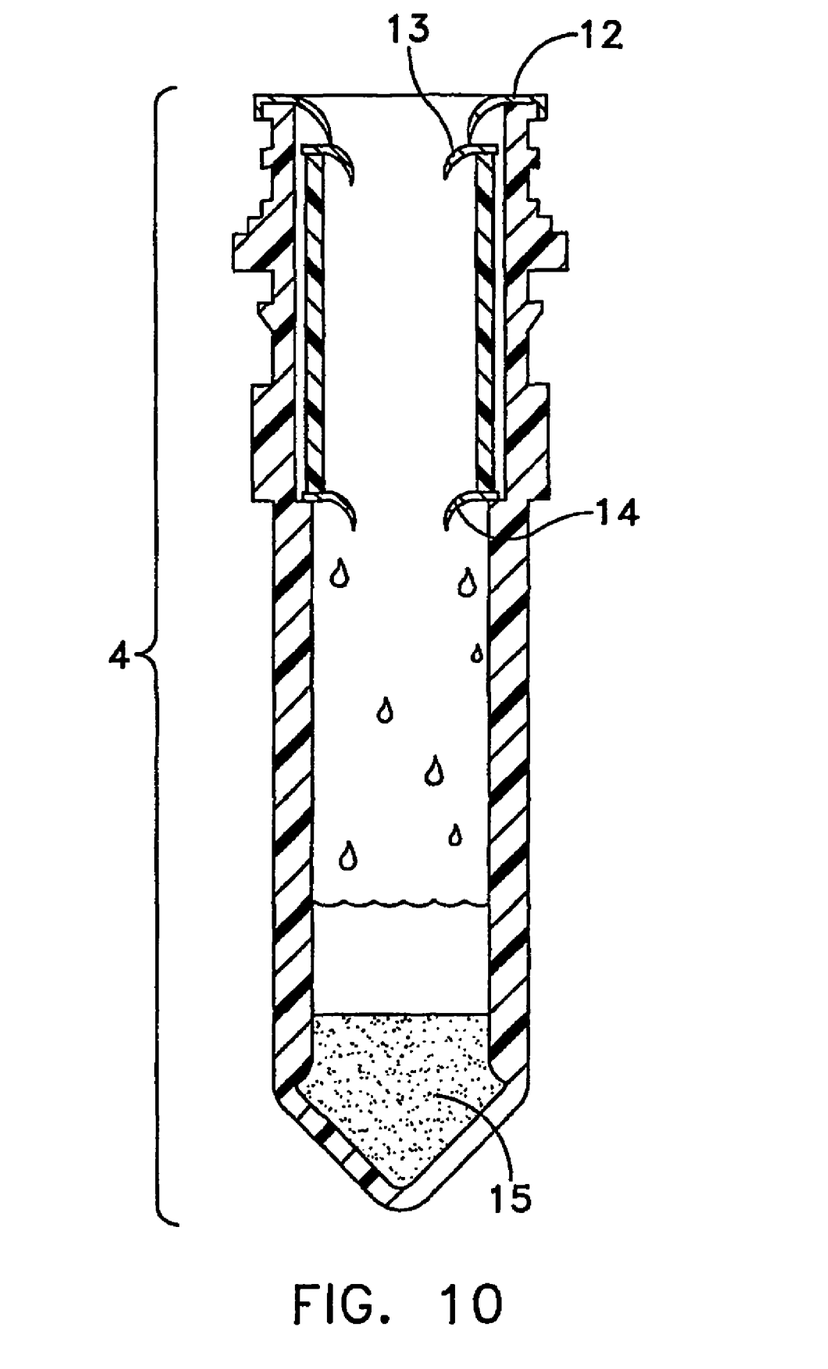
FIG. 10 is a cross-sectional view of the vial assembly 4 after the swab tip 3 has broken through all of the membrane seals 12, 13 & 14—covering the vial assembly 4, the top and bottom ends of the niblet assembly 5. The liquid, for example extractant, having already been contacted with the sample, is allowed to flow, or drip, into or onto the culture 15 at the bottom of the vial assembly 4. After sample mixing and seal puncturing the swab 1 is retracted back toward the pre-use position and does not contact the culture 15.
Figure 11:
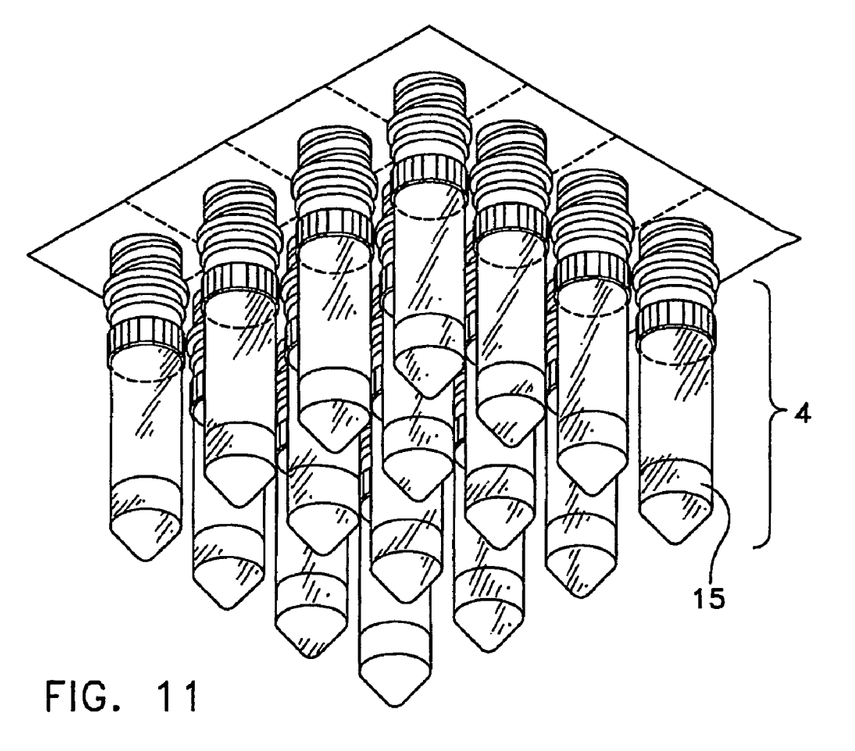
Figure 12:
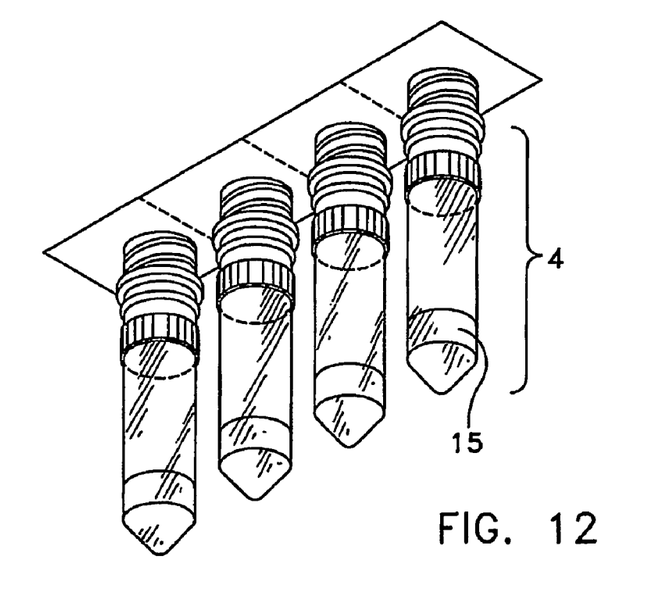

An embodiment described herein involves a user-friendly method, device and kit for the detection of a broad range of residues of antibacterial compounds in a sample such as an agricultural product. Antibiotics that may be detected include beta-lactams, sulfonamides, tetracyclines, macrolides, aminoglycosides, quinolones and amphenicols. In an embodiment, the user of the test adds the sample, incubates and observes the results.

A useful mechanism of antibiotic detection is microbial growth inhibition. Examples of microbes useful in such an application include: *B.st.; B. subtilis; B. megaterium; S. aureus; Ps. Aeuginosa; E. coli*; and *B. licheniformis*. Generally microbes which exhibit detectable growth inhibition in the presence of antibiotics may be useful. Other examples of microbial growth inhibition tests include those described in U.S. Pat. Nos. 5,354,663 and 5,489,532, the teachings of which are incorporated herein by this reference. Microbes, such as *B.st.*, that sporulate are particularly useful.

One of the benefits to microbial inhibition tests is that they can be broad spectrum compared to family or antibiotic specific antibiotic binding based tests such as those utilizing antibodies or other bacterial binders/receptors. For example, both beta-lactam and sulfonamide antibiotics will cause some inhibition of growth of *B.st*. The sensitivity of the currently available microbial inhibition tests are based on parameters including particular growth organism used, concentration of bacteria or spores, the nutrients provided and the incubation time and temperature used. Thus, in the example of *B.st.*, using one of those parameters to adjust test sensitivity may result in reduction of sensitivity to all or multiple of the antibiotics to be detected. It may be desirable, however, to reduce test sensitivity of a microbial growth inhibition assay to only certain antibiotics, or other inhibitors such as only those for which the test is overly sensitive. For example, using

*B.st.*, it may be desirable to reduce test sensitivity to only beta-lactams and not sulfonamides or other drugs or inhibitors.

In an embodiment, a binding protein isolated from bacteria, sometimes referred to as a receptor, antibiotic receptor, antibiotic binder or bacterial receptor, is utilized as an adjustment binder alone, or in combination with specific antibodies. Bacterial proteins that are sensitive to multiple antibiotics, such as a family of antibiotics, for example the beta-lactams, can allow sensitivity adjustment of multiple antibiotics to which the particular binding protein is sensitive. Antibiotic binders, such as antibodies, that are more specific, allow more specific sensitivity adjustment.

An antibiotic bound by such an adjustment reagent may be rendered unavailable, or less available, to inhibit bacterial growth. Although not wishing to be constrained by theory antibiotic binders being employed on top of agar, or other solid culture, may create large molecular weight substances that do not easily diffuse into a solid culture. Adjustment reagents, such as binders, combined into a solid culture or liquid medium, may inactivate, weaken or otherwise interfere with the antimicrobial properties or affect of the antibiotic. As such, substances other than antimicrobial binders may be useful to adjust test sensitivity including enzymes, such as beta-lactamase, that destroy antibiotic activity or otherwise inactivate antibiotics or substances that compete with antibiotics in the bacterial cell, such as analogues. One such substance is para-aminobenzoic acid (PABA), an analogue of sulfonamides with which sulfonamides compete in certain bacterial metabolic pathways. Similarly useful adjustment reagents may include substances that change the structure of an antibiotic or otherwise reduce the activity or make inactive the target antibiotic or antibiotic family. Antibiotic binders may also include non-viable bacteria or bacterial extract such as cell wall extract.

Adjustment reagents, including antibiotic binders, can be either specific to a particular drug for which the unadjusted test is overly sensitive, or have affinity to multiple drugs. The adjustment reagent may be added with the sample or premixed into a culture. One example of an adjustment reagent for multiple drugs is a microbial receptor, such as the beta-lactam receptor or receptors isolated from *B.st.* such as described in U.S. Pat. Nos. 4,239,745 and 4,239,852 the teachings of which are hereby incorporated by reference. Other possible sources of beta-lactam receptors include organisms from the genus *Bacillus* including *B. subtilis, B. megaterium*, and *B. licheniformis*. Other possible sources include *S. aureus, Ps. Aeuginosa, B. licheniformis*, and *E. coli*. Examples of useful specific adjustment reagents for particular drugs include monoclonal or polyclonal antibodies. Other examples of using antibodies for sensitivity adjustment are provided in U.S. Pat. No. 6,319,466, the teachings of which are incorporated herein by this reference.

Antibiotic binders can be isolated from bacteria and purified using known techniques. In an embodiment, beta-lactam binder isolated from *B.st.* is used to adjust the sensitivity of a microbial inhibition assay using *B.st.* as the growth organism. In such an embodiment, test sensitivity to all of the beta-lactams is reduced while test sensitivity to other antibiotics to which *B.st.* is sensitive remains relatively unaffected. This is useful, for example, when target sensitivity is European multi-residue levels (MRLs) and/or U.S. safe levels, both of which regulatory levels allow beta-lactam in tissue that may be above the levels of detection of an unadjusted *B.st.* microbial growth inhibition assay.

Other antibiotic binders that may be useful include receptors isolated from various part of bacterial or other cells including the ribosome or part of ribosome to which certain antibiotics can bind. Examples of antibiotics that bind to or otherwise inhibit ribosome function include tetracyclines, sulfonamides or fluoroquinolones. Bacterial growth inhibition by antibiotics such as tetracyclines, sulfonamides and fluoroquinolones may be adjusted by the addition of such binders. In addition, in some embodiments the adjustment reagent/binder can be an isolate from the same organism used to produce the culture.

Other useful methods of adjusting sensitivity include adding dead cells and/or crude extract that contains the desired binders/receptors.

In one embodiment, depicted in the figures, a solid culture is provided in a reagent chamber such as a vial 4 or vial-like device. Located in the same device can be a niblet 5 containing an appropriate extractant or liquid diluent 11. In an embodiment, an antibiotic binder is added to the top of the solid culture 15. In another embodiment, an antibiotic binder is mixed into the solid culture 15. In a further embodiment, the antibiotic binder is stored separately and added to the solid culture 15, along with the sample addition, prior to sample addition or soon thereafter. In another embodiment, the antibiotic binder is included pre-applied to the sampling swab 1, for example by covalently binding to the swab 1.

In an embodiment for detection of antibiotics in a sample requiring extraction, an extractant is used prior to adding the sample to the culture. An extractant that will separate antimicrobial drugs from a sample, or from a swab or other sampling device, avoids complicated extraction methods or use of organic solvents. An example of useful extractants include a combination of Trizma Base and Potassium Phosphate, such as Potassium Phosphate Monobasic in water at a pH of about 7 to about 8, for example approximately 7.5. Such an extractant buffer can be provided separately from the culture or, for ease of use, in an all in one test device such as the POCKETSWAB format 8. Using the POCKETSWAB format 8, after sample extraction the extractant (containing sample) is simply combined with the test reagents for incubation. Such extractants may extract antibiotics from the sample or merely serve to transfer the sample, including antibiotic, from the swab or other sampling device into the culture.

The POCKETSWAB format 8 is described in U.S. Pat. No. 5,965,453, which is incorporated herein by this reference. In the POCKETSWAB format 8, the extractant can be within a niblet 5. The niblet 5 can be situated within the device, above the culture 15. The niblet 5 can be sealed on the top 13 and bottom 14 ends such as with a membrane seal, for example, puncturable foil seals, on both ends to retain the buffer or extractant therein. When using the POCKETSWAB format 8, the swab 1 is removed and contacted with the sample. After sample contact, the swab 1 is used to puncture the first seal 12 (the vial 4 seal) and then the niblet top seal 12 thereby placing it within the niblet 5 and in contact with the extractant. After sufficient extraction time, the second sealed end 14 (the bottom end) of the niblet 5 is punctured allowing the contents to flow onto the culture 15. The sample is incubated at above room temperature, for example between about 60 degrees C. to about 70 degrees C., such as about 64 degrees C. Spore germination and/or bacterial growth, or lack thereof, is determined by observation of changes in growth indicators within the culture 15.

Possible growth indicators include indicators that undergo a detectable change as a function of the growth or inhibition of the culture, such as pH indicators and oxidation/reduction (redox) indicators. For example, indicators that change color in the presence of an acid or base such as to a yellowish color if the environment is acidic or purple/blue color if basic or neutral. In the case of bacterial growth, or bacterial growth following germination of spores, acid is produced. Thus, indicators will reflect creation of an increasingly acid environment as bacterial growth proceeds. If bacterial growth or spore germination is inhibited, for example by antibiotics or other inhibitors in the sample, the environment will be less acidic. The color of the acid/base indicator will reflect that relatively low acidity.

Some embodiments utilize a polybuffer. An example of such a polybuffer is a combination of buffers, one with a pKa of above 7, for example about 8 to about 11, and another with a pKa of below 7, for example about 4.5 to about 6.3. The polybuffer can be included in the culture, in a separate niblet or provided separately for later addition. When premixed in the culture, the polybuffer can be used to both stabilize the reagent system prior to test operation and stabilize results after the testing is complete.

In a particular example of a polybuffer combined with the culture, borate and succinate are used. Borate helps provide a high pH environment to stabilize the culture during pre-test storage. Succinate helps provide a low pH environment to stabilize the pH of the system after test operation. For example, in a negative sample the pH of the culture will be reduced as spores germinate and bacteria multiply. After test completion the color of the culture will reflect the test results. The buffer with pKa of below 7, for example succinate, will help stabilize the pH of the now acidic environment, thereby minimizing or preventing further color change. External pressure for pH change, for example decreased temperature after the test is removed from an incubator and the test returns to room temperature, may cause the culture to become more basic and, therefore, the test will appear more positive. A buffer with pKa below 7 will help stabilize the result even upon return to room temperature. In another embodiment Trizma Base is the high pKa buffer and can be combined with a low pKa buffer such as succinate.

Choice of buffers will be governed by a variety of factors. One factor is avoiding buffers that are particularly sensitive to the temperature changes within the test. Another factor is the starting pH of the particular buffer. For example, Trizma Base may provide less temperature stability as compared to borate. Trizma Base, however, can provide a more basic starting pH and, therefore, possibly better test sensitivity and stability as compared to borate. In an embodiment Trizma Base is used to adjust the pH of the pre-use culture to a pH of greater than about 8, for example about 10.5.

Adjusting the pH of the starting culture to a relatively high pH is also a method to improve test sensitivity and/or shelf life. A high starting pH, for example above about pH 7.5, for example about pH 8 or above, such as in the range of about pH 7.5 to about pH 11, may help prevent premature spore germination. The high pH environment may also help avoid mold contamination. Generally, the high pH environment may help extend the shelf-life of the culture prior to use.

In another embodiment multiple test samples can be tested using a test plate for example a 96 well test plate. In such an embodiment media culture and adjustment binders can be provided together in the well. In another embodiment multiple vials are supplied, for example attached to each other by a perforation or breakable plastic, so that one or multiple tests can easily supplied to the user.

Example 1

Preparation of Solid Culture (Agar Matrix)

The following culture can be used for detection of antibiotics and other inhibitors in a variety of matrices including, for example, urine, milk, water, poultry, seafood, feed and feed extracts and meat, such as kidney samples.

A Bromocresol purple (BCP)/Tris Solution was prepared by combining 25 mL of a Trizma Base solution (TBS), the solution including 2.5 grams Trizma Base in 100 mL of reverse osmosis/deionized water (RO/DI Water), with 100 milligrams of BCP and mixing well. The media was prepared by dissolving 5 grams glucose and 1 gram Mueller Hinton Broth (Mueller Hinton broth includes, in purified filtered water, 2 grams per liter (g/L) beef extract, 17.5 g/L casein hydrolysate acid and 1.5 g/L starch, pH 7.3 at 25 degrees C) into 100 mL RO/DI Water. Then a 0.01 mg/mL solution of trimethoprim in RO/DI Water was prepared and 1.2 mL was added to the media. Next 20 mL of BCP/Tris (sterile filtered through 0.45 micron filter) was added to the media.

Agar was prepared by combining 0.3 grams Difco Bacto-Agar (Item #0140-01), 0.225 NaCl and 17.485 RO/DI Water. The mixture was heated to 95° C. and then removed from the heat and allowed to cool to 75° C. Next 6 mL of media (prepared as described above with BCP/Tris) was added to the agar and mixed for 5 minutes. The mixture was cooled to 57° C. and 1 mL spore solution (concentration of 1 billion cfu/mL) was added and mixed together for 5 minutes. 0.200 mL was dispensed into the bottom of a vial 4.

Example 2

Single Service Test

The dispensed vial 4 was prepared as described in example 1. An extractant was prepared by adding 4.8 grams of 47.2% Trizma Base and 52.5% Potassium Phosphate Monobasic to 1000 mL RO/DI Water (pH should be 7.5+/−0.10). The extractant was sealed within the niblet 5 and the niblet was added to the vial 4. The vial 4 was heat sealed with foil.

Example 3

Single Service Kidney Swab Procedure (Note: this procedure is described below using a format in which the swab is provided packaged within the test unit such as in the PocketSwab.)

The single service kidney swab procedure was run by first making a 3 inch incision into kidney. The swab 1 was then withdrawn from the test unit, the test unit in the form of a POCKETSWAB, by gently pulling and twisting the handle 2 out of the test unit body 7. The swab 1 was then inserted into the incision of the kidney and allowed to sit for 15 minutes to allow full absorption of liquid into the swab 1. The swab 1 was reinserted by gently pushing down and twisting to engage the threads 6 and screwing the handle down slowly about halfway. The swab tip 3 punctured the seals 12, 13 & 14 immersing the swab tip 3 into the extractant within the niblet 5 where it sat for 2 minutes. The swab 1 was then screwed down all the way. After shaking and tapping the vial 4 to get residual liquid into the bottom of the vial 4 and in contact with the culture 15, we placed the vial 4 into a heat block set at 67° C. and incubated for 2.5 hours (if urine is tested instead of kidney, incubate for 4 hours). After 2.5 hours the vial 4 was removed from the incubator and vial color was observed in comparison to reference colors. If the negative control did not match the color specified on the protocol incubation was continued for an additional 10 minutes.

Using the above procedure with the further addition of various amounts of beta-lactam receptor units to the top of the culture, from 0.3 units to 5.0 units, test sensitivity to penicillin G, was reduced by varying amounts dependent on the amount of receptor added. See example 5 below for receptor unit determination.

Example 4

Single Service Urine Test

The culture is prepared as described in example 1. The extractant is prepared as described in example 2. The test is run the same as in example 3 except that the swab tip 3 was allowed to sit in urine sample for 10 seconds to allow full absorption into the swab tip 3 followed by incubation for 4 hours.

Example 5

Sensitivity Adjusted Single Service Kidney Test with Adjustment Binder (Receptor) Combined with Test Reagents Culture is prepared as in Example 1. Prior to dispensing 200 microliters into the vial 4, antibiotic binder is prepared, in this example an antibiotic binder from the cell wall of *B.st.*, also known as receptor. Varying amounts of inhibitory receptor units are mixed into the culture. Receptor is defined as protein removed from cellular membrane of *B.st.* A receptor unit (1 U) is the amount of receptor that will, in the test, reverse the culture growth inhibition of 12.5 ppb of penicillin G.

Receptor is useful in a variety of forms including purified form, in the form of cell paste in which receptor is a component of the whole cell or in the form of broken cell fragments.

Results from experiments are shown in Tables 1, 2 and 3.

Results in Table 1 are from tests using the culture described in Example 1 and with the addition of receptor added into rinse buffer (rinse buffer composition is 4.8 grams of 47.2% Trizma Base and 52.5% Potassium Phosphate Monobasic to 1000 mL RO/DI Water) at 0, 0.3 units (U), 1.0 U, 2.0 U, 5.0 Upper test. Sample contained the following amounts of penicillin G: 0, 5 parts per billion (ppb), 10 ppb, 12.5 ppb, 25 ppb and 50 ppb. As shown, 1.0 U was able to reverse the result of a 12.5 ppb penicillin G sample. Results are either positive (+) or negative (−).

TABLE 1

| Sample ID | 0 | 5 ppb | 10 ppb | 12.5 ppb | 25 ppb | 50 ppb |
|---|---|---|---|---|---|---|
| 0 U | − | + | + | + | + | + |
| 0.3 | − | − | − | + | + | + |
| 1.0 | − | − | − | − | + | + |
| 2.0 | − | − | − | − | + | + |
| 5.0 | − | − | − | − | + | + |

Table 2 data shows that when adding 1 U or receptor sensitivity to drugs other than beta-lactams results did not change. Results are either positive (+), negative (−) or borderline between positive and negative (+/−). Abbreviations are penicillin G (PenG); sulfamethazine (SMZ); sulfadimethoxine (SDM); tylosin (TY); gentamicin (G); oxytetracyclines (OT).

TABLE 2

| Drug and Concentration | w/out receptor | With receptor |
|---|---|---|
| Negative | − | − |
| PenG 12.5 ppb | + | − |
| PenG 25 ppb | + | + |
| SMZ 50 ppb | − | − |
| SMZ 100 ppb | +/− | +/− |
| SMZ 200 ppb | +/− | +/− |
| SDM 50 ppb | +/− | +/− |
| SDM 100 ppb | +/− | +/− |
| SDM 200 ppb | + | + |
| TY 300 | +/− | +/− |
| TY 500 | + | + |
| TY 800 | + | + |
| G 400 | +/− | +/− |
| G 600 | +/− | +/− |
| G 800 | +/− | +/− |
| OT 250 | + | + |
| OT 500 | + | + |
| OT 750 | + | + |

The results in Table 3 show that the receptor can be added to various locations or components within the test to achieve the same or similar result. Results shown are from negative sample and samples containing 12.5 ppb penicillin G and 50 ppb penicillin G. Results are either positive (+) or negative (−).

TABLE 3

| Receptor location | 0 | 12.5 ppb | 50 ppb |
|---|---|---|---|
| Control - no receptor | − | + | + |
| Receptor added to buffer | − | − | + |
| Receptor added to culture surface | − | − | + |
| Receptor added dried on swab | − | − | + |
| Receptor mixed in culture | − | − | +/− |

Example 6

Preparation of Culture Media Containing Two Buffer

The following culture can be used for detection of antibiotics and other inhibitors in a variety of matrices including, for example, urine, milk or kidney samples and can be used alone in a test container or in the single service test unit or in sensitivity adjustment examples.

BCP/Borate/Succinate Solution was prepared by adding 3.8 grams of Borate and 6 grams Succinate to 100 mL of reverse osmosis/deionized water (RO/DI Water) in 125 mL flask. 50 milligrams of BCP was added to a 50 mL conical tube and 5 mL of Borate/Succinate solution was added to the 50 milligrams BCP and mixed.

To prepare media 5 grams glucose and 1 gram Mueller Hinton Broth was dissolved in 100 mL RO/DI Water. 1.2 mL of a 0.01 mg/mL solution of trimethoprim in RO/DI Water was prepared and added to the media. A 20 mL of BCP/Borate/Succinate was added to the media and the media was sterile filtered through a 0.45 micron filter and then cooled to 4 degrees C.

Agar was prepared by combining 0.3 grams Difco Bacto-Agar (Item #0140-01), 0.225 NaCl and 17.485 RO/DI Water. The mixture was heated to 95° C. and then removed from the heat and allowed to cool to 75° C. Next 6 mL of media (prepared as described above with BCP/Tris) was added to the agar and mixed for 5 minutes. The mixture was cooled to 57° C. and 1 mL spore solution (concentration of 1 billion cfu/ mL) was added and mixed together for 5 minutes. 0.200 mL was dispensed into the bottom of each of the vials.

After dispensing, tests a run test to determine if sensitivity is adequate. If sensitivity is not adequate the procedure is repeated using either more spores (under sensitivity) or less spores (if oversensitive).

The following Table 4 shows results from antibiotic detection tests using culture described in Example 6. In test operation 200 microliters of various milk sample, spiked with known concentrations of antibiotics, were pipetted into test vials and incubated for the prescribed time (in this test 2 hours 10 minutes) and prescribed temperature (64 degrees C+/−2 degrees C.). Incubation was in the Charm I Inctronic incubator. Results were recorded immediately after test completion (Color 1) and after being left at room temperature for 16 hours (Color 2). Results listed are in parts per billion (ppb). 4 samples were run at each concentrations except for raw negative milk (16 samples) and 3 ppb pen G (2 samples) and amoxicillin (2 samples). Abbreviations are pencillin G (PenG); sulfamethazine (SMZ); sulfadimethoxine (SDM); tylosin (TY); gentamicin (G); oxytetracycline (OT); pirlimycin (Pirl); amoxicillin (Amox); ampicillin (Amp); cloxacillin (Clox); ceftiofur sodium (Ceft); cephaprin (Ceph); tilmicosin (Til); sulfadoxine (SDN); neomycin (Neo). Color result 1 and 2 is a negative result, 3 is a borderline result and 4 and 5 is a positive result.

TABLE 4

| Drug: | Conc | Color 1 | % Pos | Color 2 | % Pos | Tolerance Levels USA | EU/MRL |
|---|---|---|---|---|---|---|---|
| PenG | 4 | 5 | 100% | 5 | 100% | 5 | 4 |
| PenG | 3 | 5 | 100% | 5 | 100% | 5 | 4 |
| Amox | 6 | 5 | 100% | 5 | 100% | 10 | 4 |
| Amp | 5 | 5 | 100% | 4 | 100% | 10 | 4 |
| Clox | 30 | 4 | 100% | 5 | 100% | 10 | 30 |
| Clox | 50 | 5 | 100% | 5 | 100% | 10 | 30 |
| OT | 200 | 2 | 0% | 2 | 0% | 300 | 100 |
| OT | 300 | 5 | 100% | 4 | 100% | 300 | 100 |
| SMZ | 100 | 5 | 100% | 5 | 100% | 10 | 100 |
| SMZ | 200 | 5 | 100% | 4 | 100% | 10 | 100 |
| SDM | 25 | 4 | 100% | 5 | 100% | 10 | 100 |
| SDM | 50 | 5 | 100% | 5 | 100% | 10 | 100 |
| G | 300 | 4 | 100% | 4 | 100% | 30 | 100 |
| G | 400 | 5 | 100% | 5 | 100% | 30 | 100 |
| TY | 40 | 5 | 100% | 4 | 100% | 50 | 50 |
| TY | 50 | 5 | 100% | 5 | 100% | 50 | 50 |
| Pirl | 100 | 4 | 100% | 4 | 100% | 400 | 100 |
| Pirl | 200 | 5 | 100% | 5 | 100% | 400 | 100 |
| Ceft | 50 | 1 | 0% | 1 | 0% | 50* | 100** |
| Ceft | 100 | 2 | 0% | 2 | 0% | 50* | 100** |
| Ceph | 10 | 5 | 100% | 5 | 100% | 20 | 60 |
| SDN | 100 | 5 | 100% | 4 | 100% | NL | NL |
| Til | 80 | 5 | 100% | 5 | 100% | NL | NL |
| Neo | 750 | 5 | 100% 0% | 5 | 100% | NL | NL |
| Raw Milk: | 0 | 1 | *** | 1 | 0% | N/A | N/A |

*parent drug listed
**total parent and metabolite
***individual bulk tanker samples Example 7

Preparation of Culture Containing Two Buffer

The following culture can be used for detection of antibiotics and other inhibitors in a variety of matrices including, for example, urine, meat, poultry, seafood, milk or kidney samples and can be used in a variety of formats including single service or sensitivity adjustment examples.

A Trizma/Succinate solution was prepared by adding 2.5 grams Trizma Base and 6 grams Succinate to 100 mL of reverse osmosis/deionized water (RO/DI Water) in a 125 mL flask. 40 milligrams of BCP (see example 1 for BCP preparation) was then added to a 50 mL conical tube and 25 mL of the Trizma/Succinate solution was added to the 40 milligrams BCP and mixed.

The media was prepared by dissolving 5 grams glucose and 1 gram Mueller Hinton Broth in 100 mL RO/DI Water. 1.2 mL of a 0.01 mg/mL solution of trimethoprim in RO/DI water was added to the media. 20 mL of the BCP/Trizma/Succinate preparation was added to the media and the media was sterile filtered through a 0.45 micron filter and cooled to 4 degrees C.

0.3 grams Difco Bacto-Agar (Item #0140-01), 0.225 NaCl and 17 mL of RO/DI water was combined and mixed and heated the mixture to 95° C. The mixture was removed from the heat and allowed it to cool to 75° C. and then 6 mL media (with BCP/Tris) was added and mixed for 5 minutes. The mixture was cooled to 57° C. and 2 mL spore (concentration of 1 billion cfu/mL) was added and mixed for 5 minutes. 0.200 mL was dispensed into the bottom of each vial.

After dispensing, tests were run to determine if sensitivity was adequate. If sensitivity is not adequate the procedure is repeated using either more spores (if under sensitive) or less spores (if oversensitive).

The following Table 5 shows results from antibiotic detection tests using the culture described in Example 6. In test operation 200 microliters of various milk samples, spiked with known concentrations of antibiotics, were pipetted into vials and incubated for the prescribed time (in this test 2 hours 30 minutes) and prescribed temperature (64 degrees C. +/−2 degrees C.). Results were recorded immediately after test completion and 16 hours later. Incubation was in various Charm Inctronic I incubators. Concentrations listed are in parts per billion (ppb). 4 samples were run at each concentration except 16 negative samples were run and 2 samples each for 3 ppb pen G and amoxicillin. Abbreviations are pencillin G (PenG); sulfamethazine (SMZ); sulfadimethoxine (SDM); tylosin (TY); gentamicin (G); oxytetracycline (OT); pirlimycin (Pirl); amoxicillin (Amox); ampicillin (Amp); cloxacillin (Clox); ceftiofur sodium (Ceft); cephaprin (Ceph); tilmicosin (Til); sulfadoxine (SDN); neomycin (Neo).

TABLE 5

| Drug: | Conc | Result | % Pos | 16 hr Result | % Pos | Tolerance Levels USA | EU/MRL |
|---|---|---|---|---|---|---|---|
| PenG | 4 | Pos | 100% | Pos | 100% | 5 | 4 |
| PenG | 3 | Pos | 100% | Pos | 100% | 5 | 4 |
| Amox | 6 | Pos | 100% | Pos | 100% | 10 | 4 |
| Amp | 5 | Pos | 100% | Pos | 100% | 10 | 4 |
| Clox | 30 | Pos | 100% | Pos | 100% | 10 | 30 |
| Clox | 50 | Pos | 100% | Pos | 100% | 10 | 30 |
| OT | 200 | Pos | 0% | Pos | 0% | 300 | 100 |
| OT | 300 | Pos | 100% | Pos | 100% | 300 | 100 |
| SMZ | 100 | Pos | 100% | Pos | 100% | 10 | 100 |
| SMZ | 200 | Pos | 100% | Pos | 100% | 10 | 100 |
| SDM | 25 | Pos | 100% | Pos | 100% | 10 | 100 |
| SDM | 50 | Pos | 100% | Pos | 100% | 10 | 100 |
| G | 300 | Pos | 100% | Pos | 100% | 30 | 100 |
| G | 400 | Pos | 100% | Pos | 100% | 30 | 100 |
| TY | 40 | Pos | 100% | Pos | 100% | 50 | 50 |
| TY | 50 | Pos | 100% | Pos | 100% | 50 | 50 |
| Pirl | 100 | Pos | 100% | Pos | 100% | 400 | 100 |
| Pirl | 200 | Pos | 100% | Pos | 100% | 400 | 100 |
| Ceft | 50 | Pos | 100% | Pos | 100% | 50* | 100** |
| Ceft | 100 | Pos | 100% | Pos | 100% | 50* | 100** |
| Ceph | 10 | Pos | 100% | Pos | 100% | 20 | 60 |
| SDN | 100 | Pos | 100% | Pos | 100% | NL | NL |

TABLE 5-continued

| Drug: | Conc | Result | % 16 hr Pos | Result | % Pos | Tolerance Levels USA | EU/MRL |
|---|---|---|---|---|---|---|---|
| Tilm | 80 | Pos | 100% | Pos | 100% | NL | NL |
| Neo | 750 | Pos | 100% 0% | Pos | 100% | NL | NL |
| Raw Milk: | 0 | Neg | *** | Neg | 0% | N/A | N/A |

*parent drug only
**total parent and metabolite
***individual bulk tanker samples.

Example 8

Preparation of Culture Containing Two Buffer

The following culture can be used for detection of antibiotics and other inhibitors in a variety of formats and matrices including, for example, urine, milk or kidney samples.

BCP/Borate/Succinate solution was prepared by adding 3.8 grams of Borate and 2.7 grams Succinate to 100 mL of reverse osmosis/deionized water (RO/DI Water) in a 125 mL flask. 100 milligrams of BCP was added to a 50 mL conical tube and 25 mL of the Borate/Succinate solution was added to the 100 milligrams BCP and mixed.

To prepare the media 5 grams glucose was dissolved into 100 mL RO/DI water. 1.2 mL of a 0.01 mg/mL solution of trimethoprim in RO/DI water was added to the media along with 20 mL of the BCP/Borate/Succinate preparation. The media was sterile filtered through a 0.45 micron filter and cooled to 4 degrees C.

0.3 grams Difco Bacto-Agar (Item #0140-01), 0.225 NaCl and 18 mL of RO/DI water was combined and mixed and the mixture heated to 95° C. The mixture was then cooled to 75° C. afterm which 6 mL media was added and mixed for 5 minutes. The mixture was then cooled to 57° C. and 1 mL spore (concentration of 1 billion cfu/mL) was added and mixed in for 5 minutes. 0.200 mL was dispended into the bottom of each vial.

After dispensing, run tests to determine if sensitivity is adequate. If sensitivity is not adequate repeat procedure using either more spores (if undersensitive) or less spores (if oversensitive).

Example 9

Dispensing Culture

To efficiently dispense culture (such as is required in the previous examples), containing spores of Bst, into the bottom of the vial 4, the agar must be heated to approximately 57 degrees C. Dispensing is done rapidly, for example in less than one hour, preferably in 45 minutes or less, so that the culture can be quickly cooled. If the culture is not quickly cooled, spores, for example *B.st.* spores, may germinate prematurely. That is, spores will germinate prior to application of the sample. Excess premature germination will reduce test sensitivity.

Another method for preventing premature spore germination, which can be used alone or in conjunction with rapid dispensing, is to increase the pH of the culture, for example in the range of about pH 7.5 to about pH 11. The increase in pH provides non-optimal conditions for spore germination. The increase in pH also allows more stability over long storage times.

Example 10

Dilution Buffer

In some embodiments and examples, such as example 4, in which the sample matrix being tested is variable, a dilution buffer can be used to standardize the sample matrix. In example 4, a test for urine was described. In this example, to standardize the urine samples prior to testing the sample is diluted approximately 1 to 20 with a mixture of extractant (4.8 grams of 47.2% Trizma Base and 52.5% Potassium Phosphate Monobasic to 1000 mL RO/DI Water-pH should be 7.5+/−0.10) combined with about 8-10 grams per liter beef extract. Other samples, including feed and water can be similarly diluted (for example water was diluted 1 to 5 feed 1 to 30). By diluting the sample, test sensitivity is similarly reduced.

The invention claimed is:

1. A method for detecting the presence of at least one antibiotic in a test sample, whereby the at least one antibiotic includes a first antibiotic from a beta-lactam structural class and an antibiotic from another structural class or a second antibiotic from a beta-lactam structural class, the method comprising:
    a) combining the test sample with both a microbial culture and a microbial receptor, the culture comprising a microbial species susceptible to at least one member of the beta-lactam structural class and susceptible to at least one member of the additional antibiotic structural class or the second antibiotic from a beta-lactam structural class, the microbial receptor characterized by its sensitivity to the beta-lactam structural class, the microbial receptor having been extracted from a bacteria with sensitivity to the beta-lactam structural class, whereby contacting the susceptible microbial species with an antibiotic to which the culture is susceptible causes growth inhibition in the culture;
    b) growing the culture; and
    c) determining an amount of culture growth,
    wherein a lack of culture growth reflects a presence of an antibiotic and
    wherein the microbial receptor selectively reduces test sensitivity to the first antibiotic beta-lactam structural class without substantially reducing test sensitivity to the antibiotic from another structural class or the second antibiotic from a beta-lactam structural class.

2. The method of claim 1 further comprising extracting the antibiotic from the test sample and adding the extracted antibiotic to the culture.

3. The method of claim 2 wherein the extracting comprises adding the sample to a solution comprising a Trizma Base.

4. The method of claim 2 wherein the extracting comprises adding the sample to a solution comprising a Potassium Phosphate.

5. The method of claim 2 wherein the extracting comprises adding the sample to a solution comprising a Potassium Phosphate Monobasic.

6. The method of claim 2 wherein the extracting comprises adding the sample to a solution of a pH between about 7.0 to about 8.0.

7. The method of claim 2 wherein the extracting comprises adding the sample to a solution of a pH of about 7.5.

8. The method of claim 2 wherein the extracting comprises adding the sample to a solution comprising Potassium Phosphate Monobasic and Trizma Base at a pH of about 7.5.

9. The method of claim 1 wherein the microbial receptor is derived from the susceptible microbial species.

10. The method of claim 1 wherein the microbial receptor is added to the culture prior to adding the sample to the culture.

11. The method of claim 1 wherein the antibiotic to be detected comprises a beta-lactam.

12. The method of claim 1 wherein the microbial receptor comprises a beta-lactam binding protein.

13. The method of claim 1 wherein the microbial receptor comprises an enzyme.

14. The method of claim 1 wherein the microbial receptor comprises a beta-lactam receptor isolated from an organism of a genus *Bacillus*.

15. The method of claim 1 wherein the microbial receptor comprises a beta-lactam receptor extracted from a *Bacillus stearothermophilus*.

16. The method of claim 1 wherein growing the culture comprises incubating at above a room temperature.

17. The method of claim 1 wherein determining the amount of culture growth comprises observing a color change within the culture.

18. The method of claim 1 further comprising a colorimetric assay in which a color change reflects a change in the pH of the culture.

19. The method of claim 18 wherein a reagent for the colorimetric assay is combined within the microbial culture.

20. The method of claim 1 wherein the microbial culture comprises a bacterial spore.

21. The method of claim 1 wherein the microbial culture comprise spores of *Bacillus stearothermophilus*.

22. The method of claim 1 further comprising the step of adding to the microbial culture at least two buffers, wherein a first buffer has a pKa of above about 7 and a second buffer has a pKa of below about 7, wherein the first buffer stabilizes the pH of the culture prior to combining the sample with the microbial culture and wherein the second buffer stabilizes the pH after the determining is complete.

23. The method of claim 22 wherein one of said at least two buffers has a pKa of about 8 to about 11 and the other of said buffers has a pKa of about 4.5 to about 6.5.

24. The method of claim 22 wherein one of said buffers comprises a succinate.

25. The method of claim 22 wherein one of said buffers comprises a borate.

26. The method of claim 22 wherein one of said buffers comprises a Trizma Base.

27. The method of claim 1 wherein a pH of the microbial culture, prior to adding the sample, is above about a pH of 7.5, wherein said pH of above 7.5 stabilizes the culture prior to combining the sample with the microbial culture.

28. The method of claim 1 wherein a pH of the microbial culture, prior to adding the sample, is above about a pH of 8.0, wherein said pH of above 8.0 stabilizes the culture prior to combining the sample with the microbial culture.

29. The method of claim 1 wherein a pH of the microbial culture, prior to adding the sample, is between about a pH of 8.0 and about a pH of 10.5, wherein said pH of between 8.0 and 10.5 stabilizes the culture prior to combining the sample with the microbial culture.

* * * * *